United States Patent [19]
Bard et al.

[11] Patent Number: 4,902,620
[45] Date of Patent: Feb. 20, 1990

[54] NOVEL DNA FOR EXPRESSION OF DELTA-AMINOLEVULINIC ACID SYNTHETASE AND RELATED METHOD

[75] Inventors: Martin Bard, Menomonee Falls, Wis.; Thomas D. Ingolia, Indianapolis, Ind.

[73] Assignee: Eli Lilly and Company, Indianapolis, Ind.

[21] Appl. No.: 726,876

[22] Filed: Apr. 25, 1985

[51] Int. Cl.$^4$ .................. C12N 15/00; C12N 1/18; C12R 1/85
[52] U.S. Cl. ..................... 435/172.3; 435/255; 435/320; 435/940; 435/183; 935/28; 935/56; 935/69; 935/14; 935/64
[58] Field of Search ............. 435/172.3, 68, 317, 435/255, 256, 91, 171, 172.1, 172.3, 320, 183; 935/6, 9, 13, 22, 23, 24, 27, 28, 59, 60, 69, 14, 64

[56] References Cited

U.S. PATENT DOCUMENTS 4,588,684  5/1986  Brake .................. 435/255
4,599,311  7/1986  Kawasaki .............. 435/256

FOREIGN PATENT DOCUMENTS 2116567  9/1983  United Kingdom .......... 435/68

OTHER PUBLICATIONS

Naumduski et al., 1983 Gene 22: 203-209.
Stephién et al., 1983 Gene 24: 289-297.
Chemical Abstracts vol. 96, 1982, 96: 194407p Scarpulla et al., 1982 Anal. Biochem. 121(21:356-65.
Tuite, M.F., [66]Regulated high efficiency expression of human interferon-alpha in Saccharonyces cercuisiae, EMBO Journal vol. 1(5): pp. 603-608, 1982.
Guarente, 1987, Regulatory Proteins in Yeast, *Ann. Rev. Genet.* 21:425-452.
New England Biolabs Catalog, 1986/87, pp. 102-103.
Bard, M. and Ingolia, T. D., 1984, Gene 28: 195-199.
Labbe-Bois et al., 1983, Mitochondria, Walter de Gruyter & Co., Berlin-New York, pp. 523-534.
Arrese et al., 1983, Current Genetics 7: 175-183.
Urban-Grimal et al., 1984, Current Genetics 8: 327-331.
Rebeiz et al., 1984, Enzyme Microb. Technol. 6: 390-401.

*Primary Examiner*—Thomas G. Wiseman
*Assistant Examiner*—Richard C. Peet
*Attorney, Agent, or Firm*—Douglas K. Norman; Gerald V. Dahling; Leroy Whitaker

[57] ABSTRACT

The present invention is a novel method for maintaining and selecting recombinant DNA-containing host cells wherein the DNA encoding a selectable phenotype and the DNA encoding a useful polypeptide are the same. The aforementioned DNA is useful for expressing δ-aminolevulinic acid synthetase (ALAS) for the ultimate expression of δ-aminolevulinic acid (ALA) in yeast and related organisms. The invention further comprises plasmids pIT300, pIT301, pIT302, pIT304, pIT305, pIT306 and related Saccharomyces ALA deficient transformants. ALA is a five carbon amino acid that is useful as a light dependent herbicide.

7 Claims, 6 Drawing Sheets pIT301

Restriction Site and Function Map of Plasmid pIT301 pIT301

Restriction Site and Function Map of Plasmid pIT300 pIT300

Restriction Site and Function Map of Plasmid pIT302 pIT302

Restriction Site and Function Map of Plasmid pIT304 pIT304

Restriction Site and Function Map of Plasmid pIT305 pIT305

Restriction Site and Function Map of
Plasmid pIT306 pIT306

NOVEL DNA FOR EXPRESSION OF DELTA-AMINOLEVULINIC ACID SYNTHETASE AND RELATED METHOD

The present invention is a novel method for maintaining and selecting recombinant DNA-containing host cells wherein the DNA encoding a selectable phenotype and the DNA encoding a useful polypeptide are the same. The aforementioned DNA is useful for expressing δ-aminolevulinic acid synthetase (ALAS) for the ultimate expression of δ-aminolevulinic acid (ALA) in yeast and related organisms. The invention further comprises related recombinant DNA cloning vectors and transformants.

The development and exploitation of recombinant DNA technology has been limited by the general paucity of DNA sequences and methods for maintaining and selecting recombinant DNA-containing host cells. Selection and maintenance are important because recombinant DNA cloning vectors, such as plasmids, are often rapidly lost from host cell populations and industrial scale fermentations may require more than $10^{16}$ cells. Therefore, it is desirable that a microorganism culture containing a vector be maintained and selected so that substantially all the cells comprising the culture will contain the desired vector. This is crucial since recombinant vectors are notoriously unstable and often more than 90% of the cells in a population may not contain the vector after a culture has been grown overnight. Consequently, the productive capacity is dramatically reduced because expression of desired genes is possible only in those cells that retain the vector.

Very few effective methods have been described for maintaining and selecting recombinant DNA-containing host cells and all have serious disadvantages. One method involves incorporating antibiotic resistance genes into recombinant vectors and then adding the appropriate antibiotic to the culture medium. Cells retaining the vector with the antibiotic resistance gene are selected for and those which lose the vector are selected against. The major disadvantage of this approach is that it requires production scale growth of antibiotic resistant bacteria, use of an expensive antibiotic in the fermentation medium, and the subsequent purification to remove the antibiotic from the desired product.

Complementation of an auxotrophic mutation on the chromosome is another known method for maintaining and selecting recombinant DNA-containing host cells. As generally applied, this method severely restricts the composition of the fermentation medium and requires fermentation under media conditions which are not optimal for growth of the host cell. Therefore, this method, as in the above method of incorporating antibiotic resistance genes, requires specific manipulation of growth medium. Such manipulations increase the cost of fermentation and limit the options available for improving productivity.

The use of a lethal chromosomal marker which is repressed by a gene borne in a recombinant DNA cloning vector is also a method for maintaining and selecting recombinant DNA-containing host cells. This method has been quite effective in bacteria but is inconvenient and difficult to apply in other hosts such as yeast. The method has the additional disadvantage of requiring the use of a plasmid-borne repressor gene that does not interfere with the transcriptional activating sequence driving expression of a desired gene.

Alternative selection systems which provide for maintenance of recombinant DNA cloning vectors under all conditions of fermentation are urgently needed, especially for host cells such as yeast and related organisms. The present invention provides such a system by use of the ALAS gene, such gene allowing for the ultimate expression of ALA in yeast. ALA is normally not present in commercially available media; therefore, insertion of a vector containing the ALAS gene into a ALA deficient yeast cell provides an effective means for selecting and maintaining host cells without manipulation of the growth medium. Host cells that lose the vector are unable to grow in standard yeast media and are eliminated from the culture.

ALA is a five carbon amino acid that is effective for controlling undesirable vegetation. Therefore, not only does the ALA synthetase gene provide a means for selecting and maintaining transformed cells, but the gene simultaneously provides for expression of a useful herbicidal product. The present invention thus comprises DNA sequences, vectors, and transformants wherein the system for maintenance and selection of vectors and the production of a useful product are the same. This is highly advantageous since transformants expend energy only on the production of product and not on the components of a separate selection system. Skilled artisans will readily recognize that the expression efficiency of such transformants is greatly enhanced and that the present invention thus represents a significant advance in the technical art.

For purposes of the present invention, as disclosed and claimed herein, the following terms are as defined below.

Recombinant DNA Cloning Vector—any autonomously replicating or chromosomally integrating agent, including but not limited to plasmids, comprising a DNA molecule to which on or more additional DNA segments can or have been added.

Transformation—the introduction of DNA into a recipient host cell that changes the genotype and results in a change in the recipient cell.

Transformant—a recipient cell that has undergone transformation.

Restriction Fragment—a linear DNA molecule generated by the action of one or more restriction or other enzymes.

ALAS—δ-aminolevulinic acid synthetase.

ALA—δ-aminolevulinic acid.

ALA Deficient Cell—a cell that is unable to express δ-aminolevulinic acid in the absence of a recombinant DNA cloning vector which codes for the expression thereof.

Fused Gene Product—a recoverable polypeptide which is fused with a portion or whole of a different polypeptide.

Structural—DNA that encodes the amino acids of a functional polypeptide, such amino acids being in the correct sequential order.

DETAILED DESCRIPTION OF THE INVENTION

The present invention is a novel method for maintaining and selecting recombinant DNA-containing host cells wherein the DNA encoding a selectable and stabilizing phenotype for use in selecting and maintaining recombinant DNA vectors and the DNA encoding a useful polypeptide are the same. The aforementioned DNA encodes δ-aminolevulinic acid synthetase which is useful for the ultimate expression of δ-aminolevulinic acid in yeast.

The method thus comprises
(a) transforming a δ-aminolevulinic acid deficient Saccharomyces cell with a recombinant DNA cloning vector which codes for the expression of δ-aminolevulinic acid in said cell, and
(b) culturing the cell transformed in step (a) in a δ-aminolevulinic acid-free culture medium under conditions suitable for growth and expression of δ-aminolevulinic acid.

The invention further comprises related recombinant DNA cloning vectors and transformants.

Figure 1:
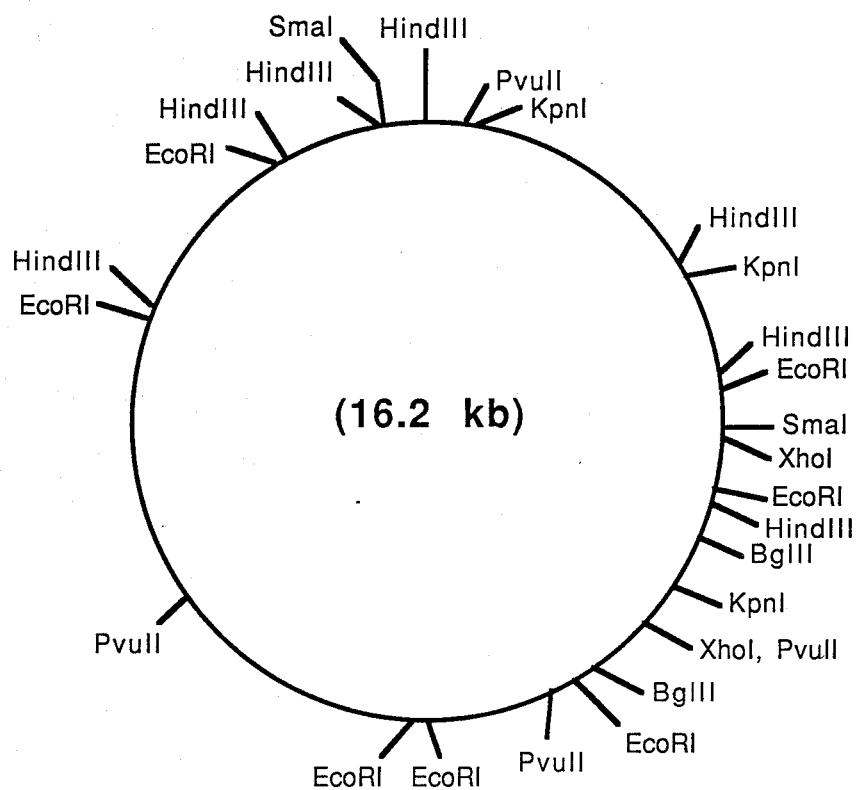
FIG. 1—Restriction Site Map of Plasmid pIT301.

The present invention can be exemplified by constructing transformants which contain an ALAS-encoding recombinant DNA cloning vector. Such a vector was constructed by ligating an ~10 kb Sau3A fragment of *Saccharomyces cerevisiae* chromosomal DNA into the unique BamHI restriction site of plasmid YEp24. The resultant ~16.2 kb vector, designated as plasmid pIT301, can be obtained from *E. coli* K12 JA221/pIT301, a strain deposited and made part of the stock culture collection of the Northern Regional Research Center, Peoria, Ill. The strain can be obtained under the accession number NRRL B-15966. The starting material plasmid YEp24, also know as pRB5, is available from the American Type Culture Collection under the accession number ATCC 37051. Yeast and related transformants containing plasmid pIT301 are illustrative of the present invention. The plasmid pIT301-containing transformants encode ALAS for the ultimate expression of ALA, such product serving as a means for maintaining and selecting plasmids and also as a herbicide for controlling undesirable weeds and vegetation. A restriction site map of plasmid pIT301 is presented in FIG. 1 of the accompanying drawings.

Figure 2:
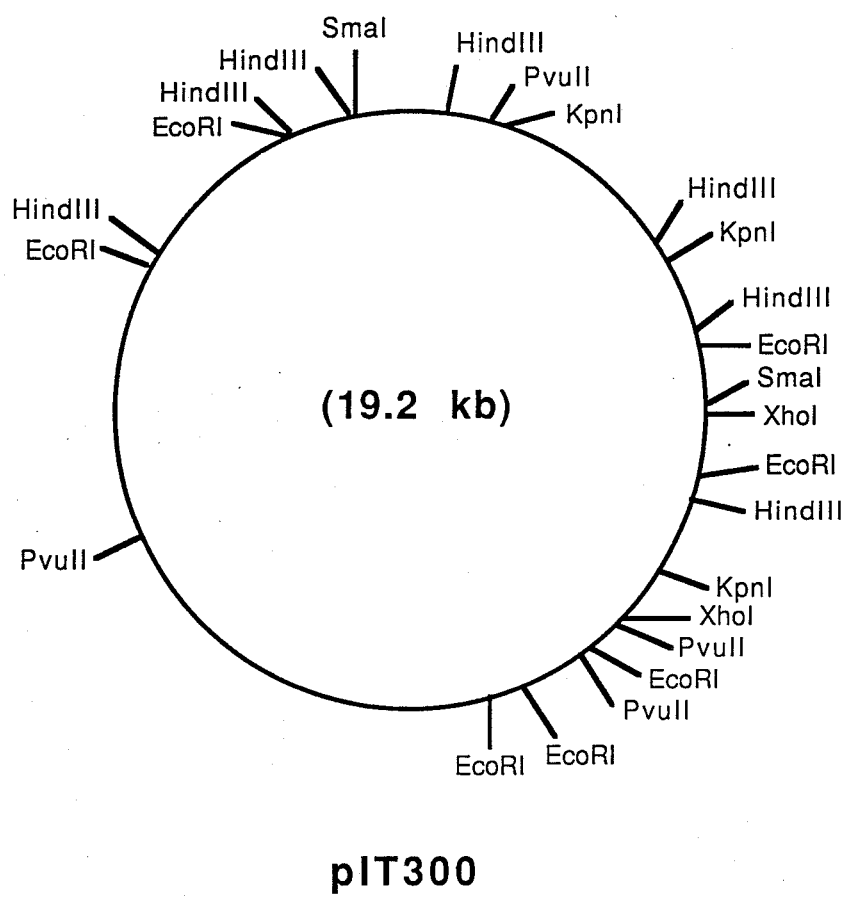
FIG. 2—Restriction Site Map of Plasmid pIT300.

Various plasmids which are functionally equivalent to plasmid pIT301 and which are useful for exemplifying the present method can also be constructed. For example, in the construction of plasmid pIT301, a different plasmid with additional DNA is inherently produced. Such plasmid, designated herein as plasmid pIT300, is colinear with pIT301 but is ~3 kb larger due to an additional ~2.5 kb of DNA at the 0 coordinate and an additional 0.5 kb of DNA at the 8.4 coordinate. Plasmids pIT300 and pIT301 can be constructed and screened for in accordance with the teaching of Example 2 herein below. Plasmids with the Sau3A insert in the reverse orientation to that shown in plasmids pIT301 and pIT300 are also produced. These plasmids are respectively designated as plasmids pIT301a and pIT300a and are functionally equivalent to plasmids pIT301 and pIT300. A restriction site map of plasmid pIT300 is presented in FIG. 2 of the accompanying drawings.

Figure 3:
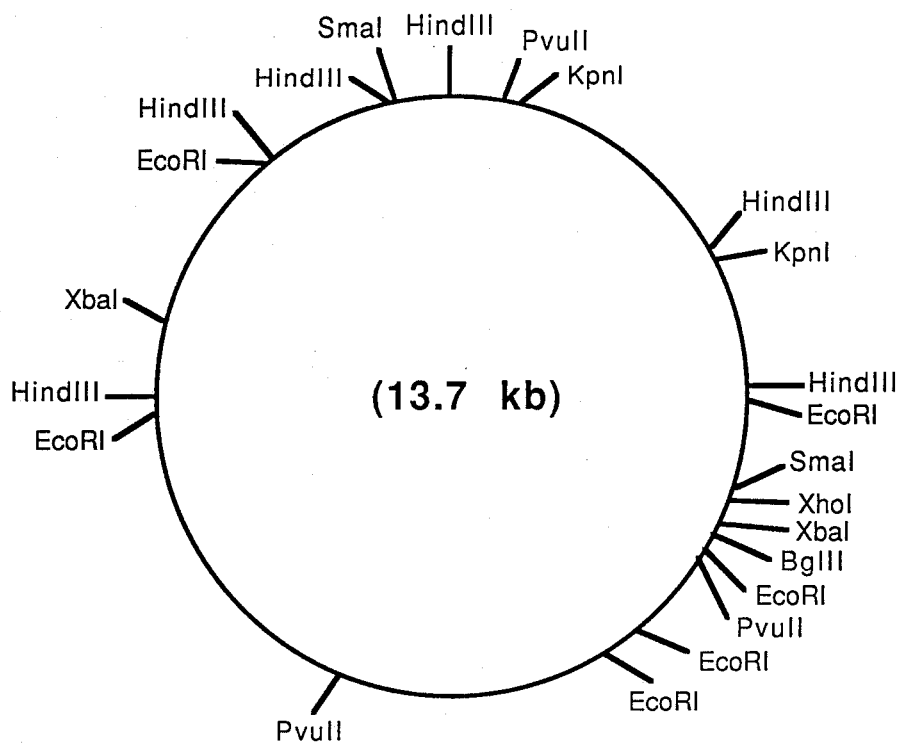
FIG. 3—Restriction Site Map of Plasmid pIT302.
Figure 4:
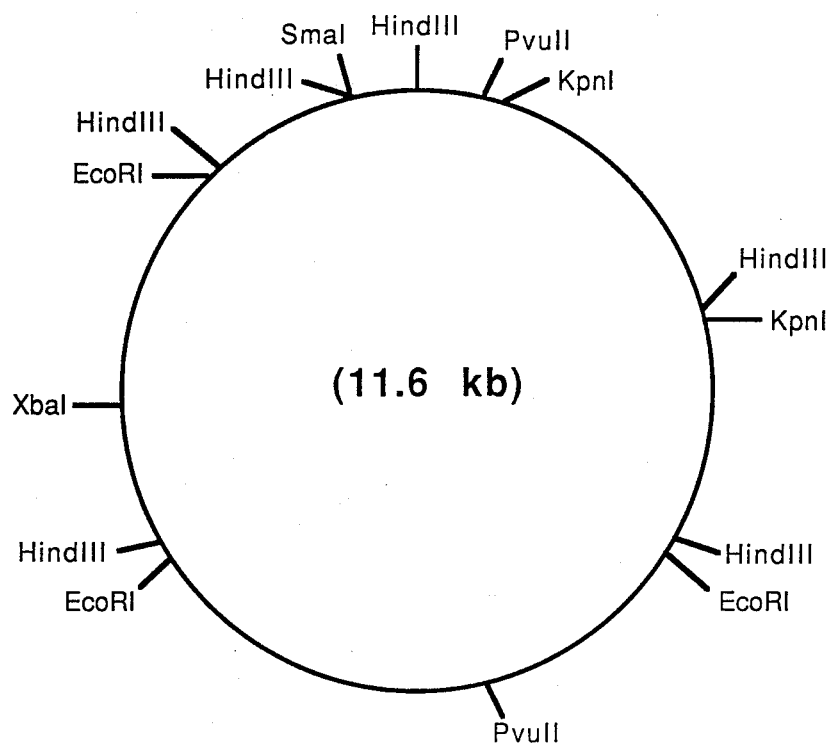
FIG. 4—Restriction Site Map of Plasmid pIT304.
Figure 5:
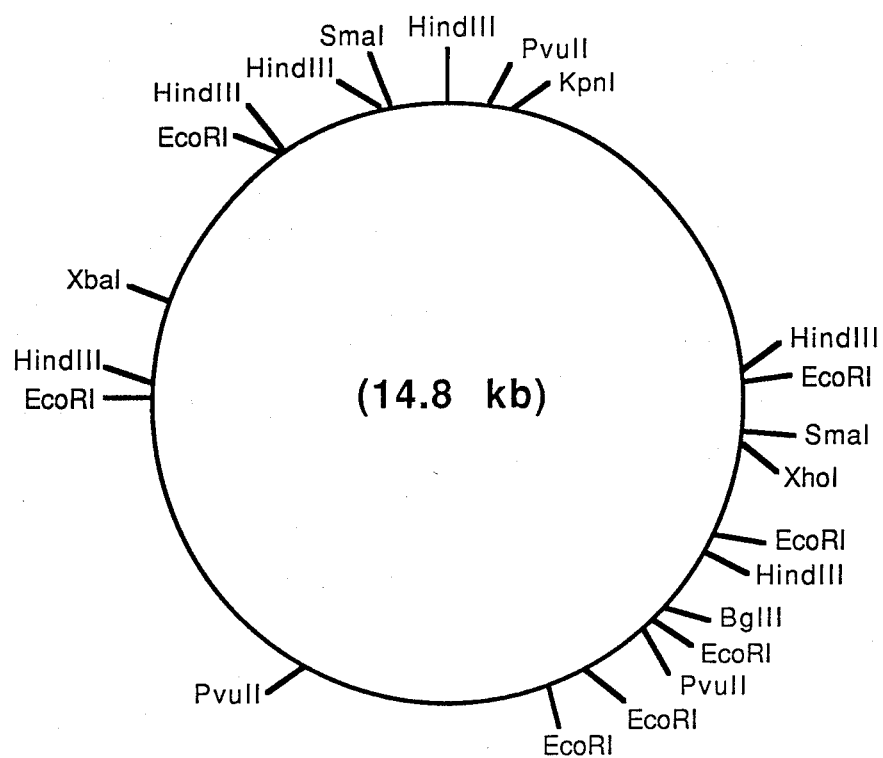
FIG. 5—Restriction Site Map of Plasmid pIT305.

Additional functionally equivalent plasmids can also be prepared by deletion within the ~8.4 kb ALAS-encoding fragment. Plasmids pIT302 and pIT305 (see FIGS. 3 and 5 respectively) were obtained after digestion of plasmid pIT301 with XhoI and BglII, respectively, followed by ligation and transformation of appropriate host cells. Both plasmids transformed ALA deficient yeast cells at high frequencies, indicating that they contained the ALAS gene. Another deletion, resulting in plasmid pIT304, was obtained after partial digestion of plasmid pIT302 with EcoRI. Plasmid pIT304 is missing four EcoRI fragments relative to plasmid pIT301 (See FIGS. 1 and 4). Since pIT304 still complemented the ALA deficiency mutation in yeast, the ALAS gene was localized to the ~3.5 kb DNA segment which remained in the insert of plasmid pIT304. Such localization was possible since KpnI digestion of plasmid pIT302 destroyed the ability of the resultant plasmid to complement this mutation. Further study indicates that the ~1.6 kb HindIII fragment of plasmid pIT304 also confers ALA activity in ALA deficient yeast.

Figure 6:
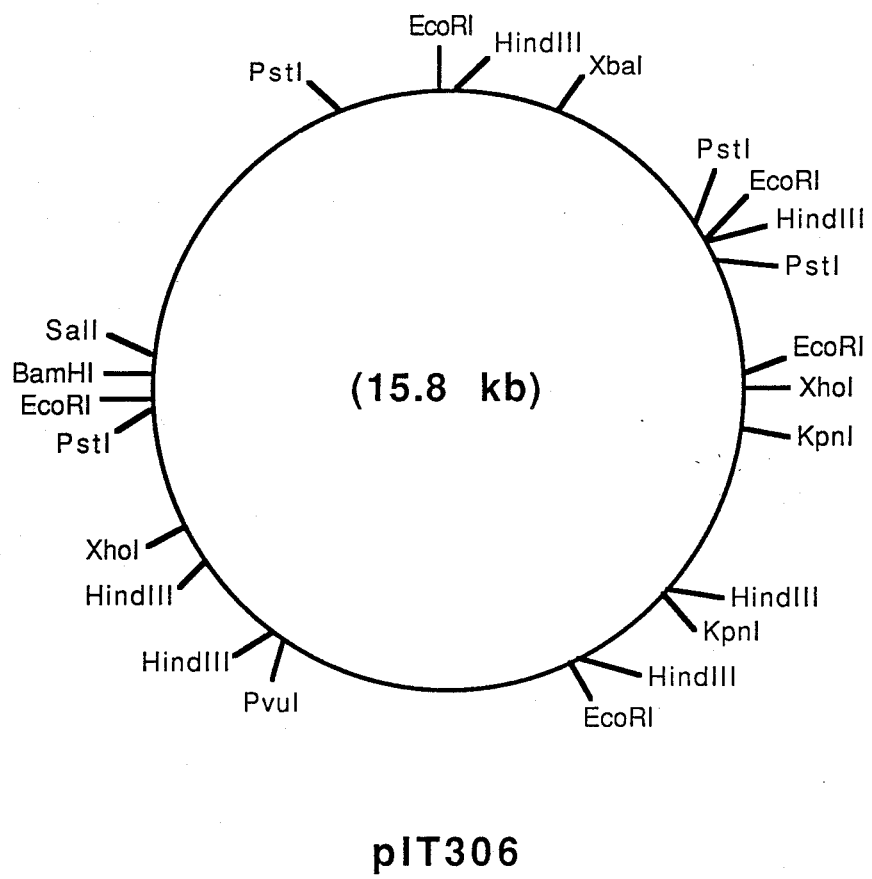
FIG. 6—Restriction Site Map of Plasmid pIT306.

Another functionally equivalent vector, plasmid pIT306, was also prepared. This plasmid was prepared by ligating the ALAS gene-containing PvuII fragment of plasmid pIT304 into the SmaI site of pIT213. The ligation inactivates the kanamycin resistance gene in plasmid pIT213. The latter plasmid can be constructed in accordance with the, teaching of Example 10 of U.S. patent application Ser. No. 535,508, attorney docket number X-6016B, filed Sept. 26, 1983, which is incorporated by reference herein. A restriction site map of plasmid pIT306 is presented in FIGS. 6 of the accompanying drawings.

The presence of ALAS activity in transformed *Saccharomyces cerevisiae* cells was determined in substantial accordance with the procedure of Arrese et al., 1983, Current Genetics, 7:175. The protocol involves permeabilizing approximately 150 mg wet weight of cells by repeated freeze-thaw followed by a colorimetric assay of accumulated ALA in substantial accordance with the method of Mauzerall and Granick, 1956, Journal of Biology and Chemistry, 219:435.

All of the aforementioned plasmids encode ALAS activity and are useful for the subsequent production and expression of ALA activity in yeast. While the plasmids are fully functional in any *Saccharomyces cerevisiae*, strains which are ALA deficient are preferred. In the latter case, ALAS expression serves as a mechanism for maintaining and selecting the plasmid while simultaneously providing for the production of an ALA product. ALA has herbicidal activity and is quite effective for eliminating or retarding the growth of unwanted vegetation.

δ-Aminolevulinic acid is widely distributed in both plant and animal cells and is a tetrapyrole precursor which induces the accumulation of various tetrapyrole intermediates of the chlorophyll biosynthetic pathway. Such intermediates comprise a heterogenous group of compounds including Pchilde, an intermediate precursor of childe a, chlorophyll a, and coproporphyrin. It has also been shown that the ALA-induced Pchilde and magnesium-porphyrin compounds consist of both monovinyl and divinyl components. Upon treatment with ALA under conditions of darkness, plants accumulate large pools of the tetrapyride intermediates. These intermediates are well tolerated when present in small amounts in plants, but are highly reactive and potentially destructive when allowed to accumulate.

Plants tolerate tetrapyrrole accumulations until exposure to sun light, after which a chain of destructive biochemical reactions occur. Triggered by sunlight, the compound pool rapidly converts triplet oxygen to the singlet form. Conversion results in a free radical chain reaction that damages plant cell membranes causing leaks, dehydration and cell death. Plants treated with ALA at night accumulate tetrapyrrole intermediates which become destructive the following morning. Therefore, ALA provides a mechanism for plants to commit suicide upon exposure to light and thus is effective as a herbicide.

The efficacy of ALA as a herbicidal compound has been tested in a variety of plants, including cucumber, lambsquarter, mustard, red-root pigweed, purslane, tomato, cotton, kidney bean, soybean, blue grass, barley, corn, crabgrass, foxtail, oats and wheat. ALA is herbicidally effective intergenerically and is not restricted to use on either monocotyledons or dicotyledons.

ALA was tested for herbicidal activity on plants grown from seed germinated in vermiculite in glass containers under standard greenhouse conditions. The natural day length was reinforced by illumination for 14 hours per day with 50 foot candles of incandescent light. Seedlings were treated after 5–28 days of growth by applying an ALA preparation as a fine spray. The ALA was dissolved in a solvent mixture made up of acetone/ethyl alcohol/0.1 Tween 80/water (0.45:0.45:0.1:9,v/v/v/v). Tween 80 is a detergent which is commercially available from Sigma Chemical Company, P.O. Box 14508, St. Louis, Mo. 63178. Each container was sprayed with 0.25 ml of solution, which is the equivalent to a spray rate of about 20 gallons per acre. After spraying, the plants were wrapped in aluminum foil and placed in a dark growth chamber at 28° C. At the end of 17 hours of dark incubation, the plants were placed in a green house and their growth evaluated over a period of 10 days. Photodynamic damage was assessed as the percent death of the sprayed tissue in response to sunlight. If 8 leaves out of sixteen sprayed leaves died as a result of exposure to daylight, the photodynamic damage was considered as 50%.

The symptoms of photodynamic damage include bleaching of the green leafy tissue and severe bleaching of the hypocotyl, often accompanied by severe loss of turgidity. At ALA concentrations of 10–20 mM (150–300g/acre), many seedlings had undergone irreversible damage after only 4 or 5 hours of exposure to daylight. Illustrative experimental results showing the herbicidal efficacy of ALA, with respect to cucumber, are presented below in Table 1.

TABLE 1

| Effect of ALA Application On Cucumber | |
|---|---|
| Treatment | Photodynamic Damage (%) |
| Control | 0 |
| 5 mM ALA | 22 |
| 10 mM ALA | 45 |
| 15 mM ALA | 95 |
| 20 mM ALA | 85 |

The present method for maintaining and selecting vectors is particularly versatile and is not limited to vectors that code exclusively for ALA. The method can also be applied to vectors which additionally code for expression of any functional polypeptide, such as, for example, human pre-proinsulin, human proinsulin, human insulin A-Chain human, insulin B-chain, human growth hormone, human growth hormone releasing factor, bovine growth hormone, human interferon, human protein C, human TPA, human urokinase, human enzyme, human hormone, and virtually any other polypeptide or protein of research or commercial value.

Although the present methods and plasmids are useful in almost all standard yeast strains, ALA deficient strains are especially advantageous. Preferred ALA deficient Saccharomyces strains include, but are not limited to, RW-1 (ole 3) and RW-2 (ole 3) and preferred ALA competent strains include DBY746 and DBY747. These strains can be obtained and are commercially available from the Yeast Genetic Stock Center, Department of Biophysics & Medical Physics, University of California, Berkeley, Calif. 94720. Other ALA deficient Saccharomyces strains can also be constructed by conventional mutagensis as described in Example 9 below.

*Saccharomyces cerevisiae* strains can best be cultured on a 1% yeast extract, 2% peptone, 5% dextrose (YEPD) medium, the components of which are commercially available from Difco Laboratories, Detroit, Mich. In the case of ALA deficient yeast strains, the aforementioned medium is supplemented with 100 mg/L ALA. For transformation, it is best to pregrow the ALA deficient strains in YEPD plus ALA followed by plating on solid (2% agar) yeast minimal medium (YMM:0.67% nitrogen base and 2% dextrose), commercially available from Difco Laboratories, Detroit, Mich. For analysis of ALAS activity, the ALA deficient cells are grown on YEPD supplemented with 1% Tween 80 and $5 \times 10^5$M ergosterol; these lipid supplements plus methionine meet the requirements for fermented growth. The present ALA deficient transformants were grown and maintained on YEPD without lipid supplements in order to maintain selection pressure for maintaining and selecting plasmids. Cells were grown to an $A_{660}$ of 10 (late log phase—$8.5 \times 10^7$ cells/ml) for enzyme analysis.

*E. coli* was cultured using standard techniques and media (LB medium: 1% tryptone, 0.5% yeast extract and 1% NaCl). Ampicillin was added at 50 μg/ml during transformation.

The following examples further illustrate the invention disclosed herein. Both an explanation of and the actual procedures for constructing the invention are described where appropriate.

EXAMPLE 1

Isolation of Plasmid pIT301

The bacterium *E. coli* K12 JA221/pIT301 (NRRL No. B-15966) was cultured in TY broth (1% tryptone, 0.5% yeast extract, 0.5% sodium chloride, pH 7.4) with 100 μg/ml of antibiotic ampicillin according to conventional micro biological procedures. After 18 hours incubation, about 0.5 ml of the culture was transferred to a 1.5 ml Eppendorf tube and centrifuged for about 15 seconds. Unless otherwise indicated, all the manipulations were done at ambient temperature. The resultant supernatant was carefully removed with a fine-tip aspirator and the cell pellet was suspended in about 100 μl of freshly prepared lysozyme solution which contained 2 μg/ml lysozyme, 50 mM glucose, 10 mM CDTA (cyclohexane diaminetetracetate) and 25 mM Tris-HCl (pH 8). After incubation at 0° C. for 30 minutes, about 200 μl of alkaline SDS (sodium dodecyl sulfate) solution (0.2N NaOH, 1% SDS) were added and the tube was gently vortexed and then maintained at 0° C. for 15 minutes. Next, about 15 μl of 3M sodium acetate (prepared by dissolving 3 moles of sodium acetate in a minimum of water, adjusting the pH to 4.8 with glacial acetic acid and then adjusting the volume to 1.1) were added and the contents of the tube gently mixed by inversion for a few seconds.

The tube was maintained at 0° C. for 60 minutes and then centrifuged for 5 minutes to yield an almost clear supernatant. About 0.4 ml of the supernatant were transferred to a second centrifuge tube to which 1 ml of cold ethanol was added. After the tube was held at −20° C. for 30 minutes, the resultant precipitate was collected by centrifugation as described above, and constituted the desired plasmid pIT301.

EXAMPLE 2

Construction of Plasmids pIT300 and pIT301 and *E. coli* JA221/pIT300 and *E. coli* JA221/pIT301

A. Isolation of DNA

Total DNA from *Saccharomyces cerevisiae* (commercially available from the Yeast Genetic Stock Center is isolated using the published procedures of Cryer et al., Methods in Cell Biology, ed. Prescott, D. M., Academic Press, N.Y., Vol. 12:39.

B. Sau3A Digestion of *Saccharomyces cerevisiae* DNA

Twenty μg of the *Saccharomyces cerevisiae* DBY939 DNA, isolated according to the teaching of Example 2A, are suspended in 200 μl of reaction mixture containing 50 mM NaCl, 6 mM Tris-HCl pH 7.5, 6 mM $MgCl_2$, and 6 mM β-mercaptoethanol. After the reaction mixture is brought to 37° C., between 0.1 and 10 units of Sau3A restriction endonuclease (New England BioLabs) are added, and the reaction is allowed to progress for between 1 and 60 minutes. The reaction is quenched by adding an equal volume of phenol:$CHCl_3$ 1:1, and vortexing. The amount of enzyme and the time of incubation is determined empirically by examining the reaction products on an agarose gel; partial cleavage products averaging 10 to 15 kb in length are desirable. After phenol:$CHCl_3$ extraction, the reaction mixture is extracted twice more with $CHCl_3$, sodium acetate is added to 0.3M, and then the DNA is ethanol precipitated, rinsed with cold 100% ethanol, and dried.

C. BamHI Digestion of Plasmid YEp24

Ten μg of plasmid YEp24 are digested in 100 μl total volume in a reaction mixture containing 150 mM NaCl, 6 mM Tris-HCl, pH 7.5, 6 mM $MgCl_2$, 6 mM β-mercaptoethanol, and 20 units of BamHI restriction endonuclease at 37° C. The completeness of reaction, reaction termination, and purification of DNA was carried out in accordance with the teachings in Example 2B.

D. Ligation and Transformation

About 100 nanograms of the BamHI cut YEp24 (described in Example 2C) is ligated with 500 nanograms of the partial Sau3A cut genomic DNA (described in Example 2B) in 50 μl as described in Example 3B below. The ligation mixture is used to transform *E. coli* JA221, again as described in Example 3B below. The resulting ampicillin-resistant transformants are pooled, and recombinant plasmid DNA is isolated from the cells in substantial accordance with the teaching of Example 1. The recombinant plasmids are then used to transform an ole3 mutant of *Saccharomyces cerevisiae* (obtained from the Yeast Genetic Stock Center as described in Example 7), except that the transformed protoplasts are regenerated in YEPD medium plus 3% agar and 1.2M soribtol. Since ole3 mutant cells cannot grow in this medium (they require ALA supplement in order to grow), only transformants containing ALAS activity, either from a plasmid-borne ALAS gene or by reversion of the ole3 mutation can grow. Cells able to grow without ALA are grown in YEPD, and plasmid DNA is prepared from the yeast cells using the procedure described below.

1. Yeast Plasmid preparation

About 30 mls of plasmid-containing yeast cells are grown in YMM under selective conditions (with ALA supplement). The cells are collected by centrifugation, washed in 4 ml of 50 mM Tris-HCl, pH 7.5, 50 mM EDTA, centrifuged again, and then resuspended in 500 μl of 20 mM Tris-HCl, pH 7.5, 150 mM NaCl, and 10 mM EDTA. About 50 μl of 100 mM DTT is added, followed by 10 μl of a 100 mg/ml Zymolyase 5000 (Zymolyase 5000 is stored at −20° C. in 20 mM Tris-HCl, pH 7.5, 150 mM NaCl, 10 mM DTT, 40% glycerol). After the reaction mixture is incubated at 37° C. for 30 minutes, the cells are lysed by addition of 50 μl of 0.5 mM EDTA and 5 μl of 10% Triton X-100; the mixture is incubated at room temperature for 15 minutes. The solution is centrifuged 15 minutes in an Eppendorf centrifuge, the pellet is discarded, and about 200 μl of 5M potassium acetate are then added. The resultant solution is incubated on ice for 30 minutes, followed by another 15 minutes centrifugation. The supernatant is extracted twice with phenol, twice with chloroform, ethanol precipitated, rinsed with 100% ethanol, and dried. The resulting 1-5 μg of plasmid DNA is then resuspended in about 50 μl water.

Plasmid DNA from the yeast transformants are then used to transform *E. coli* JA221, in substantial accordance with the teaching of Example 3B below. The desired plasmids are conventionally identified by restriction enzyme and DNA sequence analysis. A restriction site map of each of plasmids pIT301 and pIT300 is respectively presented in FIGS. 1 and 2 of the accompanying drawings.

EXAMPLE 3

Construction of Plasmid pIT302 and *E. coli* JA221/pIT302

A. XhoI Digestion

About 5 μl (5 μg) of plasmid pIT301 (isolated in Examples 1 or 2) in TE buffer (10 mM Tris-HCl, pH 8., 1 mM EDTA), 5 μl DTT (100 mM Dithiothreitol), 5 μl (1000 mg/ml) BSA (bovine serum albumin), 25 μl water, 5 μl (5 units) XhoI restriction enzyme and 5 μl 10X reaction mix* were incubated at 37° C. for about one hour. The reaction was terminated by incubation at 70° C. for 5 minutes and then the reaction mixture was cooled on ice, extracted with each of phenol and chloroform:isoamyl alcohol (24:1) and then ethanol precipitated.

* 10X Reaction mix for XhoI restriction enzyme was prepared with the following composition:
1500 mM NaCl
60 mM Tris-HCl, pH7.5
60 mM $MgCl_2$ Ligation and Transformation About 0.1 μg of the DNA of Example 3A were mixed with about 37 μl water, 5μl (10 mM) ATP, 5 μl ligation mix* and 1 μl T4 DNA ligase (~$10^5$ New England Bio Lab. Units). The mixture was incubated at 16° C. for about 16 hours and then the reaction was terminated by incubation at 70° C. for 5 minutes. After cooling on ice, the resultant ligation mixture was used to transform, in substantial accordance with the transformation procedure of Wensink, 1974, *E. coli* K12 JA221 on TY plates containing 50 μg/ml of antibiotic ampicillin. Bacterial strain *E. coli* K12 JA221 has been deposited and made part of the stock culture collection of the Northern Regional Research Laboratory, Peoria, Ill. It is available to the public under the accession number NRRL B-15211. The resultant *E. coli* K12 JA221/pIT302 transformant was used as a source of plasmid pIT302. A restriction site map of plasmid pIT302 is presented in FIG. 3 of the accompanying drawings.

* Ligation mix was prepared with the following composition:
500 mM Tris-HCl, pH 7.8
200 mM Dithiothreitol
100 mM MgCl$_2$

EXAMPLE 4

Construction of Plasmid pIT304 and *E. coli* JA221/pIT304

The desired constructions were made in substantial accordance with the teaching of Example 3 except that a partial digestion using EcoRI restriction enzyme and reaction mix*, rather than a complete digestion using XhoI restriction enzyme and reaction mix, was carried out. The desired plasmid was conventionally identified using restriction site analysis. A restriction site map of plasmid pIT304 is presented in FIG. 4 of the accompanying drawings.

* 10X Reaction mix for EcoRI restriction enzyme was prepared with the following composition:
600 mM NaCl
1000 mM Tris-HCl, pH7.5
60 mM MgCl$_2$

EXAMPLE 5

Construction of Plasmid pIT305 and *E. coli* K12 JA221/pIT305

The desired constructions were made in substantial accordance with the teaching of Example 3 except that BglII restriction enzyme and reaction mix, rather than XhoI restriction enzyme and reaction mix*, were used. The desired plasmid was conventionally identified using restriction site analysis. A restriction site map of plasmid pIT305 is presented in FIG. 5 of the accompanying drawings.

*10X Reaction mix for BglII restriction enzyme was prepared with the following composition:
600 mM NaCl
60 mM Tris-HCl, pH7.5
60 mM MgCl$_2$

EXAMPLE 6

Construction of Plasmid pIT306 and *E. coli* K12 JA221/pIT306

A. PvuII Digestion of Plasmid pIT304

The desired digestion was carried out in substantial accordance with the teaching of Example 3A except that plasmid pIT304 and PvuII restriction enzyme and reaction mix, rather than plasmid pIT301 and XhoI restriction enzyme and reaction mix, were used.

*10X Reaction mix for PvuII restriction enzyme was prepared with the following composition:
600 mM NaCl
60 mM Tris-HCl, pH 7.7
60 mM MgCl

B. SmaI Digestion of Plasmid pIT213

The desired digestion was carried out in substantial accordance with the teaching of Example 3A except that plasmid pIT213 and SmaI restriction enzyme and reaction mix, rather than plasmid pIT301 and XhoII restriction enzyme and reaction mix, were used.

*10X Reaction mix for SmaI restriction enzyme was prepared with the following composition:
200 mM KCl
60 mM Tris-HCl, pH 8.0
60 mM MgCl
60 mM β-mercaptoethanol

C. Ligation and Transformation

About 100 ng of the fragments of Example 6A and B were ligated and the resultant ligation mixture used to transform *E. coli* K12 JA221 in substantial accordance with the teaching of Example 3B. The desired plasmid was conventionally identified using restriction site analysis. A restriction site map of plasmid pIT306 is presented in FIG. 6 of the accompanying drawings.

EXAMPLE 7

Construction of *Saccharomyces cerevisiae*/pIT301

*Saccharomyces cerevisiae* cells with a mutant ole3 allele, called RW-1, (commercially available from the Yeast Genetic Stock Center) were transformed with plasmid pIT301 in substantial accordance with the teaching of Hinnen et al., 1978, Proc. Nat. Acad. Sci. USA 75:1929.

The desired construction was made by growing about 100 ml of yeast cells at 30° C. in ALA supplemented YEPD medium to an $A_{600}$ of about 1. Under sterile conditions, the cells were centrifuged and washed twice in 15 ml of 1.2M sorbitol and then resuspended in 15 ml of the sorbitol solution. After about 100 μl of 2.5 mg/ml zymolyase 60,000* (stored in 5 mM KP04, pH7.6, 1.1M sorbitol) were added, the cells were incubated at 30° C. The extent of protoplasting was monitored by adding 180 μl of 10% SDS to 20 μl aliquots and then observing under phase contrast microscopy. When about 90% of the cells appeared black, the cells were harvested by gentle centrifugation, washed twice with 15 ml of 1.2M sorbitol, resuspended in 10 ml of 1.2M sorbitol - 0.5X ALA-supplemented YEPD solution and incubated at room temperature for 40 minutes. The cells were again collected by gentle centrifugation and resuspended in 600 μl of a solution comprising ALA-supplemented 0.5X YEPD, 1.2M sorbitol, 10 mM CaCl and 10 mM Tris-HCl, pH 7.5. Aliquots (0.2 ml) of these cells were removed and added to 20 μl of a solution containing about 1 μg pIT301 DNA in 1.2M sorbitol. The mixture was incubated at room temperature for 10 minutes, at which time 1 ml of a solution comprising 20% PEG 4000**, 10 mM CaCl$_2$, 10 mM Tris-HCl, pH 7.5 was added. The mixture was incubated at room temperature for 60 minutes and then divided into four portions. Each portion was added to tubes containing 25 ml of 3% agar, 0.67% Difco yeast nitrogen base without amino acids, 1.2M sorbitol, 2% glucose, 2% YEPD and other conventional nutrients. The cells were gently mixed, immediately added to an empty sterile petri dish and, after the agar solidified, incubated at 30° C. under moist conditions. After about 3 days, ALA positive colonies were picked and streaked on YMM plates. The resultant yeast cells constituted the desired *Saccharomyces cerevisiae* RW-1/pIT301 transformants. The identity of the transformants was further confirmed by restriction enzyme and agarose gel electrophoretic analysis of the constitutive plasmids.

*Zymolyase can be obtained from the following source:
Miles Laboratory
P.O. Box 2000
Elkhart, IN 46515
**PEG 4000 can be obtained from the following source:
Baker Bioohemioals
222 Red School Lane
Phillipsburg, NJ 08865

ALA can be isolated from the transformants by lysing the cells and separating the components by conventional biochemical procedures.

EXAMPLE 8

Construction of *Saccharomyces cerevisiae* RW-1/R Wherein R is Plasmid pIT300, pIT302, pIT304, pIT305, or pIT306

The desired constructions were each independently constructed in substantial accordance with the teaching of Example 7.

EXAMPLE 9

Construction of *Saccharomyces cerevisiae* ALA Deficient Strains

The ole3 mutation from RW-1 or RW-2 can be transformed into other genetic backgrounds by mating haploid strains, creating diploids, sporulating the diploids, and isolating the haploid strains with the proper genotype. This is done by growing haploid strains of opposite mating type on YEPD plates. Next, a loopful of each strain is mixed together in liquid YEPD, incubated overnight (without shaking) at 30° C., and then streaked onto a plate that will select diploids from the background of unmated haploid cells.

To sporulate the mated cells, about 10 ml of diploid cells are grown in YEPD medium to late log ($A_{600}$ of a 1:10 dilution of about 1). The cells are washed twice in sterile water, and then resuspended in 10 mls of sterile 0.3M potassium acetate. Next, about 2 mls of these cells are placed in a sterile 20 ml tube and then 2 ml cultures of a ten fold and hundred fold dilution in 0.3M potassium acetate are set up. The cultures are incubated at 30° C. with shaking; spore formation is monitored microscopically. Four spores are contained in a tetrahedral structure called an ascus which is approximately $\frac{1}{3}$ to $\frac{1}{2}$ the size of a yeast cell. The efficiency and rapidity of spore formation is strain dependent; typically, 5 to 50 percent of the cells will be sporulated in 2-5 days. The spores are stable in this liquid culture for months at 4° C. The spores are then dissected with a micromanipulater or by the method of Munz, P., Methods in Cell Biology, ed., Prescott, T., Vol 9:185. Haploid strains derived from the spores are grown in YEPD supplemented with ALA, and the genotypes checked to determine which haploids have the desired genetic background.

EXAMPLE 10

Construction of ALA-Deficient *Saccharomyces cerevisiae*/R Wherein R is Plasmid pIT300, pIT301, pIT302, pIT304, pIT305, or pIT306, The desired ALA-deficient yeast transformants are independently constructed in substantial accordance with the teaching of Example 7.

We claim:

1. A method for maintaining and selecting a recombinant DNA-containing Saccharomyces cell comprising:
   (a) transforming a delta-aminolevulinic acid deficient Saccharomyces cell with a recombinant DNA cloning vector carrying a gene encoding delta-amino-levulinic acid synthetase, expression of which results in the production of delta-aminolevulinic acid in said transformed cell, and
   (b) culturing the cell transformed in step (a) in a delta-aminolevulinic acid-free culture medium under conditions suitable for growth and expression of said gene encoding synthetase, wherein said recombinant DNA cloning vector is selected from the group consisting of plasmid pIT300, pIT301, pIT302, pIT304, pIT305, and pIT306.

2. The plasmid of claim 1 which is plasmid pIT301.
3. The plasmid of claim 1 which is plasmid pIT302.
4. The plasmid of claim 1 which is plasmid pIT304.
5. The plasmid of claim 1 which is plasmid pIT305.
6. The cell of claim 1 which is *Saccharomyces cerevisiae*/pIT301.
7. The cell of claim 1 which is *Saccharomyces cerevisiae* RW-l/pIT304.

* * * * *

UNITED STATES PATENT AND TRADEMARK OFFICE
CERTIFICATE OF CORRECTION

PATENT NO. : 4,902,620

DATED : February 20, 1990

INVENTOR(S) : Martin Bard and Thomas D. Ingolia

It is certified that error appears in the above-identified patent and that said Letters Patent is hereby corrected as shown below:

In Claim 1, line 12, after "encoding" please add -- delta aminolevulinic acid --.

Signed and Sealed this

Twenty-sixth Day of February, 1991

Attest:

HARRY F. MANBECK, JR.

*Attesting Officer*   *Commissioner of Patents and Trademarks*